United States Patent [19]

Peffly et al.

[11] Patent Number: 6,149,898

[45] Date of Patent: *Nov. 21, 2000

[54] HAIR STYLING COMPOSITIONS CONTAINING SILICONE MICROEMULSIONS AND CATIONIC NON-POLYMERIC LIQUIDS

[75] Inventors: Marjorie Mossman Peffly, Cincinnati; Dennis Eugene Kuhlman, Middletown, both of Ohio

[73] Assignee: The Procter & Gamble Company, Cincinnati, Ohio

[*] Notice: This patent is subject to a terminal disclaimer.

[21] Appl. No.: 09/102,039

[22] Filed: Jun. 22, 1998

[51] Int. Cl.$^7$ ............................... A61K 7/06; A61K 7/00
[52] U.S. Cl. .................... 424/70.12; 424/70.1; 424/7.11; 424/401; 424/78.02
[58] Field of Search ............................... 424/401, 70.11, 424/70.1, 70.12, 78.02

[56] References Cited

U.S. PATENT DOCUMENTS

| | | | |
|---|---|---|---|
| 3,766,267 | 10/1973 | Zak et al. | 260/561 B |
| 4,584,356 | 4/1986 | Crivello | 525/479 |
| 4,659,777 | 4/1987 | Riffle et al. | 525/100 |
| 4,689,289 | 8/1987 | Crivello | 430/270 |
| 4,693,935 | 9/1987 | Mazurek | 428/352 |
| 4,728,571 | 3/1988 | Clemens et al. | 428/352 |
| 4,733,677 | 3/1988 | Gee et al. | 132/7 |
| 4,871,529 | 10/1989 | Sramek | 424/47 |
| 5,017,221 | 5/1991 | Legrow et al. | 106/2 |
| 5,032,460 | 7/1991 | Kantner et al. | 428/449 |
| 5,244,598 | 9/1993 | Merrifield et al. | 252/314 |
| 5,362,485 | 11/1994 | Hayama et al. | 424/70 |
| 5,380,528 | 1/1995 | Alban et al. | 424/401 |
| 5,468,477 | 11/1995 | Kumar et al. | 424/78.17 |
| 5,523,365 | 6/1996 | Geck et al. | 526/194 |
| 5,578,298 | 11/1996 | Berthiaume et al. | 424/70.122 |
| 5,618,524 | 4/1997 | Bolich, Jr. et al. | 424/70.12 |
| 5,658,557 | 8/1997 | Bolich, Jr. et al. | 424/70.12 |
| 5,658,577 | 8/1997 | Fowler et al. | 424/401 |
| 5,891,954 | 4/1999 | Gee et al. . | |
| 5,965,115 | 10/1999 | Bolich, Jr. et al. . | |
| 5,968,495 | 10/1999 | Bolich, Jr. et al. . | |
| 5,972,356 | 10/1999 | Peffly et al. . | |
| 5,985,294 | 11/1999 | Peffly . | |
| 5,985,295 | 11/1999 | Peffly . | |
| 5,997,886 | 12/1999 | Peffly et al. . | |

FOREIGN PATENT DOCUMENTS

| | | | |
|---|---|---|---|
| 0268982 A2 | 6/1988 | European Pat. Off. | A61K 7/06 |
| 0459500 B1 | 12/1991 | European Pat. Off. | C08G 77/10 |
| 0463431 A2 | 1/1992 | European Pat. Off. | C08J 3/03 |
| 0560516 A1 | 9/1993 | European Pat. Off. | A61K 7/06 |
| 95/23581 | 9/1995 | WIPO . | |
| 9714395 A1 | 4/1997 | WIPO | A61K 7/06 |

OTHER PUBLICATIONS

"The Use of Living Radical Polymerization to Synthesize Graft Copolymers," Beers et al., Polymer Preprints, pp. 571–572, Mar. 1996.

Macromolecular Design: Concepts & Practice, M.K. Mishra, Ed., 1994, Chapter 8.

Development of Novel Attachable Initiator for Living Radical Polymerization and Synthesis of Polysiloxane Block Copolymer, Y. Nakagawa and K. Matyjaszewski, pp. 270–271, Polymer Preprints, Aug. 1996.

Polymer Handbook, $2^{nd}$ Edition, J. Brandrup and E.H. Immergut, Eds., Section IV, pp. 337–348, 1975.

Chemistry and Technology of Silicones, Walter Noll, pp. 373–376, 1968.

"New Formulation Possibilities Offered by Silicone Copolyols," G.H. Dahms and A. Zombeck, Cosmetics & Toiletries, pp. 91–100. vol. 110, Mar. 1995.

Primary Examiner—Thurman K. Page
Assistant Examiner—Brian K. Seidleck
Attorney, Agent, or Firm—William J. Winter; Lucy Elandjian

[57] ABSTRACT

Disclosed are hair styling compositions comprising from about 0.01% to about 20% of a non-silicone-containing hair styling polymer; from about 0.1% to about 20% of a liquid hydrophilic non-polymeric cationic compound having at least one quaternary ammonium moiety; from about 3% to about 99% of selected carriers; and an organopolysiloxane microemulsion that contains a dispersing surfactant and from about 0.01% to about 10% organopolysiloxane (by weight of the composition), wherein the organopolysiloxane is substantially free of amino groups in combination with hydroxyl groups and the microemulsion has an average particle size of less than about 80 nm. The composition provides good style retention, restyling benefits, and improved hair aesthetics, e.g. blacker/shinier hair, less sticky/stiff.

36 Claims, No Drawings

HAIR STYLING COMPOSITIONS CONTAINING SILICONE MICROEMULSIONS AND CATIONIC NON-POLYMERIC LIQUIDS

TECHNICAL FIELD

The present invention relates to personal care compositions, especially hair styling compositions, containing a liquid hydrophilic non-polymeric cationic compound containing at least one quaternary ammonium moiety, and silicone microemulsions. The invention further relates to stable hair styling compositions containing a liquid hydrophilic non-polymeric cationic compound containing at least one quaternary ammonium moiety, a silicone microemulsion, and a lower monohydric alcohol.

BACKGROUND OF THE INVENTION

The desire to have the hair retain a particular style or shape is widely held. Many vehicles for accomplishing this have been found including mousses, gels, lotions and spray compositions, typically dispensed from a mechanical pump spray device or pressurized aerosol canister. Such compositions provide temporary setting benefits and can usually be removed by water or by shampooing. The materials used in these types of hair styling compositions are generally resins, gums, and adhesive polymers which are capable of imparting style or shape to the hair. Many of these products also contain lower alcohols in order to obtain good films of the polymer in a short period of time.

Many people desire a high level of style retention, or hold, from a hair styling product. In addition, in some areas of the world consumers desire a hair styling composition that also provides improved hair aesthetics and a restyle benefit. For example, many people in China tend to have very damaged hair because of low conditioner usage, cut their hair less frequently than Western consumers and have more environmental negatives (hard water, pollution, etc.). This damage causes hair to appear dull. Therefore, most of these consumers equate improved aesthetics, e.g. blacker, shinier hair, with healthier and more beautiful hair. Furthermore, the ability to restyle hair without additional product application is desired in many areas of the world because of the low shampoo frequency and the high cost (vs. income) of hair styling compositions.

Unfortunately, most hair styling products having good hold characteristics suffer from the disadvantage of not providing good hair aesthetics. Silicones tend to minimize stiffness and stickiness and provide a desirably smooth or soft hair feel. Unfortunately, silicone emulsions tend to be difficult to formulate in hair styling compositions. Hair styling compositions tend to be complex, requiring a number of ingredients for different purposes, with potential for incompatibilities. For example, silicone emulsions tend to be unstable in compositions containing lower alcohols, resulting in phase separation of the composition. Other incompatibilities in the system, e.g., polymer-polymer or polymer-surfactant interactions, can also result in phase separation. This phase separation is not only undesirable for visual aesthetic reasons, but for performance reasons as well. When the product phase separates, hold and/or hair feel properties of the product tend to be negatively impacted. Furthermore, those products providing improved aesthetics suffer from the disadvantage of tradeoffs in product performance (i.e. hold) and product form (i.e. foaming).

Therefore, a need exists for hair styling compositions providing style retention with improved hair aesthetics without tradeoffs in product performance or product form. Furthermore, a need exists for a product that incorporates all of these attributes and provides a restyle benefit.

It has surprisingly been found that stable hair styling compositions providing these benefits and containing up to about 55% monohydric alcohol can be provided by employing a combination of (i) a non-silicone containing hair styling polymer, (ii) an optional plasticizer, (iii) a silicone microemulsion substantially free of a combination of amino groups and hydroxyl groups and having a specific particle size, namely less than about 80 nm, (iv) a liquid hydrophilic non-polymeric cationic compound containing at least one quaternary ammonium moiety, and (v) certain solvent systems for the hair styling polymer.

It is therefore an object of this invention to provide stable hair styling compositions containing a liquid hydrophilic non-polymeric cationic compound containing at least one quaternary ammonium moiety, and silicone microemulsions, especially compositions which also contain lower alcohols.

It is another object of this invention to provide hair styling compositions that provide good style retention. It is another object of this invention to provide hair styling compositions that provide improved hair aesthetics without tradeoffs in product performance or product form. Another object of this invention is to provide hair styling compositions that both look and feel natural.

It is another object of this invention to provide methods for styling and holding hair. Another object of this invention is to provide hair styling compositions that provide a restyle benefit without tradeoffs in product performance or product form.

These and other objects will become readily apparent from the detailed description which follows.

SUMMARY OF THE INVENTION

The present invention relates to personal care compositions, especially hair styling compositions, comprising from about 0.01% to about 20% of a non-silicone containing polymer suitable for hair styling; an organopolysiloxane microemulsion wherein the amount of microemulsion is such that the personal care composition comprises from about 0.01% to about 10% of organopolysiloxane; from about 0.1% to about 20% of a liquid hydrophilic non-polymeric cationic compound containing at least one quaternary ammonium moiety; and from about 3% to about 99% of a carrier. The polysiloxane microemulsion in turn comprises an organopolysiloxane dispersed as particles in the microemulsion, wherein the organopolysiloxane is substantially free of amino groups in combination with hydroxyl groups, has an average particle size of less than about 80 nanometers, and has a surfactant system for dispersing the organopolysiloxane in the microemulsion that is compatible with the hair styling polymer. The carrier in turn comprises from about 3% to about 99%, by weight of the composition, of a first solvent selected from the group consisting of water; water soluble organic solvents; organic solvents which are strongly to moderately strong in hydrogen-bonding parameter; and mixtures thereof; wherein the first solvent is other than $C_1$–$C_3$ monohydric alcohol, $C_1$–$C_3$ ketone and $C_1$–$C_3$ ether, and optionally, from about 0% to about 55% of a second solvent selected from the group consisting of $C_1$–$C_3$ monohydric alcohols, $C_1$–$C_3$ ketones, $C_1$–$C_3$ ethers, and mixtures thereof.

It has been found that the compositions of the present invention provide good hair style retention and aesthetics in the presence of lower alcohols. It has also been found that incorporation of select styling polymers and plasticizers, as defined herein, provides a restyle benefit in addition to the good style retention and improved hair aesthetics.

DETAILED DESCRIPTION OF THE INVENTION

The essential components of the present invention are described below. Also included is a nonexclusive description of various optional and preferred components useful in embodiments of the present invention.

The present invention can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All molecular weights are weight average molecular weights and are given in units of grams per mole.

All solubility parameters are given in Hilderbrand units (H) which are equivalent to $(cal\text{-}cm^{-3})^{1/2}$.

All ingredient levels are in reference to the active level of that ingredient, and are exclusive of solvents, by-products, or other impurities that may be present in commercially available sources, unless otherwise indicated.

All measurements made are at ambient room temperature, which is approximately 73° F., unless otherwise designated.

All documents referred to herein, including all patents, patent applications, and printed publications, are hereby incorporated by reference in their entirety in this disclosure.

The term "suitable for application to human hair" and the like, as used herein, means that the compositions or components thereof so described are suitable for use in contact with human hair and the scalp and skin without undue toxicity, incompatibility, instability, allergic response, and the like.

The components of the compositions hereof are selected such that the total composition will be compatible. As used herein, compatible means there is no marked phase separation, e.g., excessive cloudiness, layering or precipitation of the composition which negatively impacts the esthetic or functional properties of the composition in a significant manner.

Preferred compositions are those wherein the mixture of hair styling polymer, silicone microemulsion, and carrier is a substantially homogeneous solution or dispersion (preferably microdispersion), more preferably substantially clear to translucent in appearance. Preferred final compositions are those also characterized by these properties.

Preferred compositions are those wherein the mixture of essential components provide a % transmittance of at least about 50% at a wavelength of 460 nm as determined by standard spectroscopy methods. Preferred final compositions are those also characterized by these properties.

Hair Styling Polymers

The composition of the present invention comprises a non-silicone containing hair styling polymer for providing stylability to the hair. Hair styling polymers possess adhesive properties such that they are capable of shaping or styling the hair, and should be removable by shampooing or rinsing the hair. One or more hair styling polymers may be used. The total amount of hair styling polymer is generally from about 0.01% to about 20%, preferably from about 0.1% to about 15%, more preferably from about 0.5% to about 10%. A variety of hair styling polymers are suitable in the present invention. Particular polymers will be selected by the skilled artisan considering the solubility of the polymer in the composition and the ionicity of the composition.

Suitable hair styling polymers are those which are soluble or dispersible in the carrier described herein in the ratios employed in the composition such that the polymer forms a substantially homogeneous solution or dispersion (preferably a microdispersion) with the carrier. Solubility/dispersibility is determined at ambient conditions of temperature and pressure (25° C. and 101.3 kPa (1 Atm)). Solubility/dispersibility of the polymer should be determined after neutralization, if any.

Suitable non-silicone-containing hair styling polymers include nonionic, anionic, cationic, and amphoteric polymers, and mixtures thereof. The non-silicone-containing hair styling polymers are preferably present in a combined amount of from about 0.01% to about 20%, more preferably from about 0.1% to about 15%, and most preferably from about 0.5% to about 10% by weight of composition.

Suitable cationic polymers include Polyquaternium-4 (Celquat H-100; L200-supplier National Starch); Polyquaternium-10 (Celquat SC-240C; SC-230 M—supplier National Starch); (UCARE polymer series—JR-125, JR-400, LR-400, LR-30M, LK, supplier Amerchol); Polyquaternium-11 (Gafquat 734; 755N—supplier ISP); Polyquaternium-16 (Luviquat FC 370; FC550; FC905; HM-552 supplier BASF); PVP/Dimethylaminoethylmethacrylate (Copolymer 845; 937; 958-ISP supplier); Vinyl Caprolactam/PVP/Dimethylaminoethyl Methacrylate copolymer (Gaffix VC-713; H2OLD EP-1—supplier ISP); Chitosan Lactate (Kytamer L—supplier Amerchol); Chitosan PCA (Kytamer PC—supplier Amerchol); Polyquaternium-7 (Merquat 550—supplier Calgon); Polyquaternium-18 (Mirapol AZ-1 supplied by Rhone-Poulenc); Polyquaternium-24 (Quatrisoft Polymer LM-200—supplier Amerchol); Polyquaternium-28 (Gafquat HS-100—supplier ISP); Polyquaternium-46 (Luviquat Hold—supplier BASF); and Chitosan Glycolate (Hydagen CMF; CMFP—supplier Henkel); Hydroxyethyl Cetyldimonium Phosphate (Luviquat Mono CP—supplier BASF); and Guar Hydroxylpropyl Trimonium Chloride (Jaguar C series -13S, -14S, -17, 162,-2000, Hi-CARE 1000—supplier Rhône-Poulenc).

Preferred cationic polymers are Polyquaternium-4; Polyquaternium-10; Polyquaternium-11; Polyquaternium-16; PVP/Dimethylaminoethylmethacrylate; Vinyl Caprolactam/PVP/Dimethylaminoethyl Methacrylate copolymer; Chitosan Lactate; and Chitosan PCA.

Suitable amphoteric polymers include Octylacrylmide/Acrylates/Butylaminoethyl Methacrylate Copolymer (Amphomer 28-4910, Amphomer LV-71 284971, Lovocryl-47 28-4947—National Starch supplier), and Methacryloyl ethyl betaine/methacrylates copolymer (Diaformer series supplier Mitsubishi). Preferred are Octylacrylmide/Acrylates/Butylaminoethyl Methacrylate Copolymer.

Especially preferred polymers for relatively low alcohol systems (e.g., less than about 55% alcohol) are those which are partially zwitterionic in that they always possess a positive charge over a broad range of pH but contain acidic groups which are only negatively charged at basic pH. Therefore the polymer is positively charged at lower pH and neutral (have both negative and positive charge) at higher pHs. The zwitterionic polymer may be selected from cellulose derivatives, wheat derivatives and chitin derivatives such as are known in the art. Nonlimiting examples of zwitterionic polymers useful herein include Polyquaternium-47 (Merquat 2001—supplier Calgon (a zwitterionic copolymer of acrylic acid, methacryl amido propyl trimethyl ammonium chloride, and methyl acrylate)); Carboxyl Butyl Chitosan (Chitolam NB/101—marketed by Pilot Chemical Company, developed by Lamberti); and Dicarboxyethyl Chitosan (N-[(3'-hydroxy-2',3'-dicarboxy) ethyl]-beta-D-(1,4)-glucosamine) (available from Amerchol as, e.g., CHITOLAM NB/101).

Useful nonionic polymers include PVP or Polyvinylpyrrolidone (PVP K-15, K-30, K-60, K-90, K-120—supplier ISP) (Luviskol K series 12, 17, 30, 60, 80, & 90—supplier BASF); PVP/VA Copolymer (PVP/VA series S-630; 735, 635, 535, 335, 235—supplier ISP) (Luviskol VA); PVP/DMAPA acrylates copolymer (Styleze CC-10—supplier ISP); PVP/VA/Vinyl Propionate copolymer (Luviskol VAP 343 E, VAP 343 I, VAP 343 PM—supplier BASF); Hydroxylethyl Cellulose (Cellosize HEC—supplier Amerchol); and Hydroxylpropyl Guar Gum (Jaguar HP series -8, -60, -105, -120—supplier Rhône-Poulenc).

Preferred nonionic polymers are PVP or Polyvinylpyrrolidone; PVP/VA Copolymer; PVP/DMAPA acrylates copolymer; and Hydroxylpropyl Guar Gum.

Anionic polymers suitable for use herein include VA/Crotonates/Vinyl Neodecanonate Copolymer (Resyn 28-2930—National Starch supplier); Butyl Ester of PVM/MA (Gantrez A-425; ES-425; ES-435—supplier ISP); Ethyl Ester of PVM/MA (Gantrez ES-225; SP-215—supplier ISP); Acrylates/acrylamide copolymer (Luvimer 100P; Lumiver Low VOC, supplier BASF); Methacrylate Copolymer (Balance 0/55—National Starch supplier); Vinyl Acetate/Crotonic Acid copolymer (Luviset CA 66—supplier BASF); Isopropyl Ester of PVM/MA Copolymer (Gantrez ES-335—supplier ISP); Acrylates Copolymer; Methacrylates/acrylates copolymer/amine salt (Diahold polymers—supplier Mitsubishi); 2-Butenedioic Acid (Z)-, Monoethyl Ester, Polymer with Methoxyethene (Omnirez 2000); VA/Butyl maleate/Isobornyl Acrylate (Advantage Plus terpolymer—supplier ISP); Acrylates Copolymer (Amerhold DR-25—supplier Amerchol); Acrylates/Hydroxyesteracrylates Copolymer (Acudyne 255 supplier Rohm & Haas); vinyl Acetate/Crotonic Acid/Vinyl Propionate copolymer (Luviset CAP—supplier BASF); PVP/Acrylates copolymer (Luviflex VBM 35—supplier BASF); Diglycol/CHDM/Isophthalates/SIP Copolymer (Eastman AQ 48, AQ 55—supplier Eastman Chemicals); Acrylates/Octacrylamide Copolymer (Versatyl-42 or Amphomer HC—National Starch supplier); TBA/AA copolymer (75/25—Mitsubishi Chemical Corp.); Acrylates Copolymer (Aculyn 33—supplier Rohm & Haas); Acrylates/Steareth-20 Methacrylate Copolymer (Aculyn 22—supplier Rohm & Haas); and Carbomer (supplier B.F. Goodrich).

Preferred anionic polymers are VA/Crotonates/Vinyl Neodecanonate Copolymer; Butyl Ester of PVM/MA; Ethyl Ester of PVM/MA; Acrylates/acrylamide copolymer; Methacrylate Copolymer; and Vinyl Acetate/Crotonic Acid copolymer.

The compositions herein may contain a plasticizer for the hair styling polymer. Any plasticizer suitable for use in hair care products or for topical application to the hair or skin can be used. A wide variety of plasticizers are known in the art. One or more plasticizers may be used. It has been found that these plasticizers, when added to personal care compositions containing styling polymers at an adequate level, especially the preferred styling polymers described below, provide restyle benefits in addition to good style retention and improved hair aesthetics without the disadvantages of stiff or sticky compositions.

In the context of plasticizers herein, "hydrophilic" refers to any compound with a solubility parameter of at least about 12.7 (i.e. it is at least soluble in 100% ethanol at 20° C.), additionally the compound should also be fully soluble in the final composition. When restyle is desirable, plasticizers are generally used at levels of from about 0.01% to about 250%, preferably at least about 100%, more preferably at least about 150%, and most preferably at least about 200%, by weight of the polymer.

Preferred polymers for combination with plasticizers for restyle include those polymers comprising at least one monomer of vinyl pyrrolidone. Specific examples include PVP, PVP/VA Copolymer and Polyquaternium-11. Preferred polymers for combination with plasticizers for restyle also include those polymers comprising at least one monomer of hydroxyethylcellulose. Specific examples include Polyquaternium-4 and Polyquaternium-10. Preferred polymers for combination with plasticizers for restyle further include those polymers comprising at least one chitin moiety. Specific examples include Chitosan Lactate and Chitosan PCA.

Preferred plasticizers for use herein include those plasticizers that are organic, hydrophilic compounds. Preferred plasticizers further include those plasticizers that are humectants. Also preferred are plasticizers that are organic, hydrophilic compounds and further comprise at least one hydroxyl group. Specific examples include glycerine, propylene glycol, dipropylene glycol, and diethylene glycol.

Organopolysiloxane Microemulsions

The compositions of the present invention contain an organopolysiloxane microemulsion comprising polysiloxane particles dispersed in a suitable carrier (typically aqueous) with the aid of a surfactant. The organopolysiloxane is substantially free of, preferably essentially free of, more preferably contains no, organopolysiloxane having both amino groups and hydroxyl groups. The microemulsions are preferably included in an amount such that the composition contains from about 0.01 to about 10% of the dispersed polysiloxane, more preferably about 0.05% to about 6%, most preferably about 0.1% to about 4%.

Organopolysiloxane microemulsions can be produced by the emulsion polymerization of organosiloxane having a low degree of polymerization in a solvent comprising water. The organopolysiloxane is stabilized in the microemulsion by a surfactant, e.g., a nonionic surfactant and an ionic surfactant. The average particle size of the emulsion after emulsion polymerization (corresponding to the organopolysiloxane in the emulsion) is less than about 80 nanometers (nm), preferably less than about 60 nm, more preferably less than about 40 nm. Particle size of a microemulsion can be determined by conventional methods, e.g., using a Leeds & Northrup Microtrac UPA particle sizer. Microemulsions having these particle sizes are more stable and have better external appearance than those having larger particle sizes. Furthermore, the degree of polymerization (DP) of the polysiloxane after emulsion polymerization is preferably in the range of from 3 to 5,000, more preferably in the range of from 10 to 3,000.

The organopolysiloxane in the microemulsion can be a linear or branched chain siloxane fluid having a viscosity of about 20–3,000,000 $m^2$/s (cs), preferably 300–300,000 cs, more preferably 350–200,000 cs, at 25° C.

Suitable organopolysiloxanes may contain the difunctional repeating "D" unit:

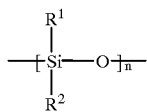

wherein n is greater than 1 and $R^1$ and $R^2$ are each independently $C_1$–$C_7$ alkyl or phenyl. A mixture of siloxanes may be used. Exemplary siloxanes include polydimethylsiloxane, polydiethylsiloxane, polymethylethylsiloxane, polymethylphenylsiloxane, and polydiphenylsiloxane. Siloxane polymers with dimethylsiloxane "D" units are preferred from an economic standpoint. However, $R^1$ and $R^2$ may independently be a functional group other than methyl, e.g., carboxyalkyl, haloalkyl, acrylate, acryloxy, acrylamide, vinyl or mercaptoalkyl.

The siloxane may be terminated with hydroxy groups, alkoxy groups such as methoxy, ethoxy, and propoxy, or trimethylsiloxy groups, preferably hydroxy or trimethylsiloxy.

The emulsion can be prepared by the emulsion polymerization process described in EP 459500 (published Dec. 4, 1992), incorporated herein by reference. In that process, stable, oil free polysiloxane emulsions and microemulsions are prepared by mixing a cyclic siloxane, a nonionic surfactant, an ionic surfactant, water, and a condensation polymerization catalyst. The mixture is heated and agitated at polymerization reaction temperature until essentially all of the cyclic siloxane is reacted, and a stable, oil free emulsion or microemulsion is formed. The reaction mix, especially surfactant levels, and conditions are controlled in order to provide the desired organopolysiloxane particle size. The emulsions and microemulsions typically have a pH of about 3 to about 10 (e.g., 6–7.5), and contain about 10 to about 70% by weight siloxane polymer, preferably about 25 to about 60%, about 0% to about 30% by weight nonionic surfactant, about 0% to about 30% by weight ionic surfactant, preferably about 0% to about 20%, the balance being water. Preferred emulsions and methods of making them are further described in U.S. patent application Ser. No. 08/929,721, filed on Sep. 15, 1997 now U.S. Pat. No. 5,891,984 in the names of Ronald P. Gee and Judith M. Vincent, incorporated herein by reference in its entirety.

Microemulsions can also be produced by the emulsion polymerization process described in EPA 0268982, published Jun. 6, 1988, assigned to Toray, incorporated herein by reference in its entirety. In this process, the microemulsion is prepared by a process in which a crude emulsion, consisting of polysiloxane having a low degree of polymerization, a first surfactant (anionic, cationic, and nonionic surfactants), and water, is slowly dripped into an aqueous solution containing a catalytic quantity of a polymerization catalyst and a second surfactant which acts as an emulsifying agent (which may be the same as the first surfactant, however, the surfactants should be compatible in the reaction mixture considering the ionicity of the reaction mixture). The reaction mix and conditions are controlled to provide the desired organopolysiloxane particle size. Therefore, a dropwise addition of the crude emulsion into the aqueous solution of catalyst and surfactant of 30 minutes or longer is preferred in order to produce microemulsions having smaller particle sizes. In addition, the quantity of surfactant used in the catalyst plus the surfactant aqueous solution is from about 5 to about 70 weight %, more preferably from about 25 to about 60 per 100 weight parts polysiloxane in the crude emulsion.

Any conventional nonionic surfactant can be used to prepare the microemulsion. Exemplary types of nonionic surfactants include silicone polyethers, both grafted and linear block, ethoxylated fatty alcohols, ethoxylated alcohols, ethoxylated alkyl phenols, Isolaureth-6 (polyethylene glycol ether of branched chain aliphatic $C_{12}$ containing alcohols having the formula $C_{12}H_{25}(OCH_2CH_2)_6OH$), fatty acid alkanolamides, amine oxides, sorbitan derivatives (e.g., commercially available from ICI Americas, Inc., Wilmington, Del., under the tradenames SPAN and TWEEN), and propylene oxide-ethylene oxide block polymers (e.g., commercially available from BASF Corp., Parsippany, N.J. under the trademark PLURONIC). Ionic surfactants useful in preparing the microemulsion include any conventional anionic surfactant such as sulfonic acids and their salt derivatives. Ionic surfactants also include any conventional cationic surfactant used in emulsion polymerization. Surfactants of these types are well known in the art and are commercially available from a number of sources. Specific examples of these surfactant types are also disclosed in the above referenced patent application Ser. No. 08/929,721 now U.S. Pat. No. 5,891,954.

The surfactant can be used in the form of a single type of surfactant (e.g., anionic, cationic or nonionic), or the surfactant can be used as a combination of two or more types provided that they are compatible with each other and the other components of the composition. Preferred combinations of surfactant types include the combination of two or more types of anionic surfactants, the combination of two or more types of nonionic surfactants, the combination of two or more types of cationic surfactants, the combination of two or more types of surfactants selected from both the anionic and nonionic surfactants; and the combination of two or more types of surfactants selected from both the cationic and nonionic surfactants.

The catalyst employed in the emulsion polymerization may be any catalyst capable of polymerizing cyclic siloxanes in the presence of water, including condensation polymerization catalysts capable of cleaving siloxane bonds. Exemplary catalysts include strong acids and strong bases, ionic surfactants such as dodecylbenzenesulfonic acid, phase transfer catalysts, and ion exchange resins where a catalyst is formed in situ. As will be understood by those skilled in the art, a given surfactant may also serve as the polymerization catalyst (e.g., alkylbenzenesulfonic acids, or quaternary ammonium hydroxides or salt thereof may function as both a surfactant and the polymerization catalyst).

A surfactant system, catalyst and resulting microemulsion suitable for use in the compositions of the present invention can be selected by the skilled artisan considering the ionicity of the composition. In general, these materials are selected such that the total composition will be compatible.

The silicone microemulsion may contain a silicone polyether copolyol, such as described herein. Alternatively or additionally, the compositions hereof may contain a silicone polyether. If the microemulsion is supplied as a material not containing a silicone polyether already present in the emulsion, a silicone polyether may be added prior to making the batch composition hereof. Where the polyether is not dispersible in the silicone microemulsion, it is preferably mixed in about an equal portion of water containing from 10–50% $C_1$–$C_3$ monohydric alcohol, preferably ethanol, prior to combination with the silicone microemulsion. This pre-mix is then added to the other ingredients of the composition which have preferably been pre-mixed.

Organopolysiloxane microemulsions are available from a number of commercial sources.

The following organopolysiloxane microemulsions are manufactured by Dow Corning of Midland, Mich.:

Microemulsions containing dimethicone copolyol:

| Microemulsion Trade Name | Si Type | Internal phase viscosity (cps) | Surfactant | Si particle. Size, nm |
|---|---|---|---|---|
| DC 2-5791 | Dimethyl-siloxanol, Dimethyl cyclo-siloxane | 70–90 M | Triethanolamine dodecylbenzene sulfonate, Polyethylene oxide lauryl ether | <50 |
| DC 2-5791 - sp | Dimethyl-siloxanol, Dimethyl cyclo-siloxane | 70–90 M | Triethanolamine dodecylbenzene sulfonate, Polyethylene oxide lauryl ether | <40 |
| DC 2-5932 | Dimethyl-siloxanol, Dimethyl cyclo-siloxane | 1–2 M | Cetrimonium Chloride, Trideceth-12 | <30 |

Microemulsions not containing dimethicone copolyol:

| Micro-emulsion Trade Name | Si Type | Internal phase viscosity (cps) | Surfactant | Si particle. Size, nm |
|---|---|---|---|---|
| DC 2-1470 | Dimethyl-siloxanol, Dimethyl cyclo-siloxane | 15–20 M | Triethanolamine dodecylbenzene sulfonate, Polyethylene oxide lauryl ether | <50 |
| DC 2-1845 | Dimethyl-siloxanol, Dimethyl cyclo-siloxane | 4–8 M | Triethanolamine dodecylbenzene sulfonate, Polyethylene oxide lauryl ether | <40 |
| DC 2-1845 HV | Dimethyl-siloxanol, Dimethyl cyclo-siloxane | 60–70 M | Triethanolamine dodecylbenzene sulfonate, Polyethylene oxide lauryl ether | <35 |
| DC 2-1550 | Dimethyl-siloxanol, Dimethyl cyclo-siloxane | 100–600 M | Triethanolamine dodecylbenzene sulfonate, Polyethylene oxide lauryl ether | ≦50 |
| DC 2-1281 | Dimethyl-siloxanol, Dimethyl cyclo-siloxane | 1–2 M | Cetrimonium Chloride, Trideceth-12 | <30 |
| DC 2-8194 | Dimethyl, aminomethyl propyl siloxane | 4–6 M | Cetrimonium Chloride, Trideceth-12 | ≦30 |
| DC 2-1716 MEM | Dimethyl-siloxanol with methyl silsequi-oxane, Octamethyl cyclotretra siloxane | 10–30 M | Cetrimonium Chloride, Trideceth-12 | 50–80 |

Where the composition contains a hair styling polymer which is an anionic acrylate polymer, DC 2-1845 and DC 2-5791 are preferred microemulsions. When the hair styling polymer is a cationic polymer comprising nitrogen, the DC 2-8194, DC2-1281, and/or DC 2-5932 microemulsions are preferred.

Liquid Hydrophilic Non-Polymeric Cationic Compound

The composition of the present invention comprises a liquid hydrophilic non-polymeric cationic compound containing at least one quaternary ammonium moiety. Such cationic compounds are well known in the art. It has been found that these cationic compounds, when added to the personal care compositions defined herein, provide improved hair aesthetics, e.g. blacker hair, which correlates with consumer perception of healthy hair.

In this context, "liquid" refers to those compounds that are liquid at about 20° C. As used herein, and unless otherwise specified, "hydrophilic" refers to those compounds which have a solubility parameter of at least about 14 (i.e. it is at least soluble in an 88% ethanol/12% water mixture at 20° C.), additionally it is desirable for the compound to be fully soluble in the final composition. The concentration of liquid hydrophilic non-polymeric quaternary ammonium compound in the composition is generally from about 0.1% to about 20%, preferably from about 0.1% to about 10%, more preferably from about 0.1% to about 5%.

It is believed the liquid hydrophilic compound provides improved aesthetics by laying down damaged hair cuticles against the hair shaft. This process of laying the cuticles down is believed to change the angle of reflection for light allowing the natural colors of the hair to be reflected more accurately while allowing the silicon to provide shine to the hair. This compound is not a surfactant for the purpose of providing a surfactant system to the silicone microemulsion.

Preferred liquid hydrophilic non-polymeric compounds include those compounds containing at least one quaternary ammonium moiety and at least one glycosyl moiety. Specific examples include Laureth Methyl Gluceth—10-Hydroxylpropyl Dimonium Chloride (Gluquat 100 or Gluquat 125—supplier Amerchol) and Quaternium-22 (Glucoamidopropyl Dimethyl-2-hydroxyethyl Ammonium Chloride; Ceraphyl 60—supplier ISP). The most preferred compound is Quaternium-22 (Glucoamidopropyl Dimethyl-2-hydroxyethyl Ammonium Chloride; Ceraphyl 60—supplier ISP).

Preferred liquid hydrophilic non-polymeric compounds also include those compounds containing at least one quaternary ammonium moiety and at least one alkylene oxide moiety. Specific examples include PPG-40 Diethylmonium Chloride (Emcol CC55—supplier Witco); PEG-15 Cocomonium Chloride (Variquat K1215—supplier Witco); PEG-2 Cocomonium Chloride (Variquat 638—supplier Witco); PPG-9 Diethylmonium Chloride (Emcol CC9—supplier Witco); and PPG-40 Diethylmonium Chloride (Emcol CC42—supplier Witco). Preferred liquid hydrophilic non-polymeric compounds further include those compounds containing at least one quaternary ammonium moiety and at least one ethyl sulfate moiety. Specific examples include Coamidopropyl Ethyldimonium Ethosulfate (Schercoquat CAS); Stearamidopropyl Ethyldimonium Ethosulfate (Schercoquat SAS—supplier Scher Chemicals); Isostearamidopropyl Ethyldimonium Ethosulfate (Schercoquat IAS—supplier Scher Chemicals); Isostearyl Ethyl Imidonium Ethosulfate (Schercoquat IIS—supplier Scher Chemicals); Quaternium-61 (Schercoquat DAS—supplier Scher Chemicals); Soyamidopropyl Ethyldimonium Ethosulfate (Schercoquat SOAS—supplier Scher Chemicals); Saffloweramidopropyl Ethyldimonium Ethosulfate (Schercoquat FOAS—supplier Scher Chemicals); Rapeseedamidoproyl Ethyldimonium Ethosulfate (Schercoquat ROAS—supplier Scher Chemicals); Apricotamidopropyl Ethyldimonium Ethosulfate (Schercoquat APAS—supplier Scher Chemicals); Wheatgermamidopropyl Ethyldimonium Ethosulfate (Schercoquat WOAS—supplier Scher Chemicals); and Canolamido Propyl Ethyl Dimonium Ethosulfate (Schercoquat COAS—supplier Scher Chemicals).

Preferred liquid hydrophilic non-polymeric compounds include those compounds containing at least one quaternary ammonium moiety and at least one epoxypropyl chloride moiety. Specific examples include Quaternium-62 (Schercoquat IEP) and Rapeseedamidopropyl Epoxypropyl Dimonium Chloride (Schercoquat ROEP).

Preferred liquid hydrophilic non-polymeric compounds include those compounds containing at least one quaternary ammonium moiety and an ester moiety selected from the group consisting of lauryl acetyl moieties and isostearyl acetyl moieties. Specific examples include Di-Lauryl Acetyl Dimonium Chloride (Schercoquat ALA—supplier Scher Chemicals) and Isostearamidopropyl Laurylacetodimonium Chloride (Schercoquat IALA—supplier Scher Chemicals).

Preferred liquid hydrophilic non-polymeric compounds include those compounds containing at least one quaternary ammonium moiety and at least one ethoxy chloride moiety.

A specific example is alkyl C12–C18 dimethyl ammonium ethoxy chloride.

Carrier

The compositions of the invention also comprise a carrier for the hair styling polymer and the silicone microemulsion. Suitable carriers are those in which the hair styling polymer is soluble or dispersible, preferably soluble or microdispersible, and wherein the organopolysiloxane of the microemulsion is dispersible. Choice of an appropriate carrier will also depend on the particular end use and product form contemplated (e.g., the hair styling polymer to be used, and the product form, e.g., for hair styling compositions such as hair spray, mousse, tonic, lotion or gel). The carrier is preferably suitable for application to the hair.

The carrier is present at from about 0.5% to about 99.5%, preferably from about 5% to about 99.5%, most preferably from about 50% to about 95%, of the composition.

The compositions of the present invention comprise one or more suitable solvents for the hair styling polymer. Preferred solvent systems are those which form a homogeneous solution or dispersion (preferably microdispersion) with the hair styling polymer in the weight ratios used in the composition. Preferred solvent systems are those which form a substantially clear to translucent solution or dispersion (preferably microdispersion) with the hair styling polymers in the weight ratios used in the composition.

Preferred solvents include those selected from the group consisting of water; water soluble organic solvents; organic solvents which are strongly to moderately strong in hydrogen-bonding parameter; and mixtures thereof; wherein the solvent is other than $C_1$–$C_3$ monohydric alcohol, $C_1$–$C_3$ ketone and $C_1$–$C_3$ ether. Water is a preferred solvent. At least about 3% to about 99%, preferably at least about 5% to about 98%, of this type of solvent is used in the composition.

Exemplary water soluble organic solvents other than $C_1$–$C_3$ monohydric alcohols, $C_1$–$C_3$ ketones and $C_1$–$C_3$ ethers include propylene glycol, glycerine, phenoxyethanol, dipropylene glycol, sugars, and mixtures thereof.

Solvents which are moderately strong to strong in hydrogen-bonding parameter other than $C_1$–$C_3$ monohydric alcohols, $C_1$–$C_3$ ketones and $C_1$–$C_3$ ethers include esters, ethers, ketones, glycol monoethers (moderately H-bonded) and alcohols, amines, acids, amides and aldehydes (strongly H-bonded). A description and examples of solvents of this type are disclosed in Polymer Handbook, 2d. Ed., J. Brandrup and E. H. Immergut, Editors, John Wiley & Sons, N.Y., 1975, Section IV, page 337–348 (Table 2). Preferred solvents of this type are dibutyl phthalate, propylene carbonate, propylene glycol monomethyl ether, methyl acetate, methyl proprionate and mixtures thereof. Propylene glycol monomethyl ether, methyl acetate, methyl proprionate and mixtures thereof are preferred; methyl acetate is most preferred.

Other solvents suitable for use herein are water soluble, organic volatile solvents selected from $C_1$–$C_3$ monohydric alcohols, $C_1$–$C_3$ ketones, $C_1$–$C_3$ ethers, and mixtures thereof, monohydric alcohols being preferred. Preferred solvents of this type are methylal, ethanol, n-propanol, isopropanol, acetone and mixtures thereof. More preferred are ethanol, n-propanol, isopropanol, and mixtures thereof. Where the composition comprises about 40% or more of such solvents, at least about 5% of water, a water soluble organic solvent, and/or an organic solvent which is strongly to moderately strong in hydrogen-bonding parameter is used.

In a preferred embodiment, the carrier comprises (i) a solvent selected from the group consisting of water; water soluble organic solvents; organic solvents which are strongly to moderately strong in hydrogen-bonding parameter; and mixtures thereof; wherein the solvent is other than $C_1$–$C_3$ monohydric alcohol, $C_1$–$C_3$ ketone and $C_1$–$C_3$ ether; (ii) a solvent selected from the groups consisting of $C_1$–$C_3$ monohydric alcohols, $C_1$–$C_3$ ketones, $C_1$–$C_3$ ethers, and mixtures thereof; and (iii) mixtures thereof; preferably a mixture thereof. Especially preferred are a mixture of water and $C_1$–$C_3$ monohydric alcohol, e.g., water-ethanol or water-isopropanol-ethanol. Another particularly preferred solvent system comprises one or more of propylene glycol monomethyl ether, methyl acetate, and methyl proprionate, preferably methyl acetate, optionally with one or more of water or a $C_1$–$C_3$ monohydric alcohol.

The carrier may include other solvents, e.g., hydrocarbons (such as isobutane, hexane, decene, acetone), halogenated hydrocarbons (such as Freon), linalool, volatile silicon derivatives, especially siloxanes (such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof.

Solvents used in admixture may be miscible or immiscible with each other. However, in the final composition such solvents should be compatible with each other and other components in the composition such that solids do not precipitate.

Reduced "volatile organic compound" or "VOC" compositions may be desirable. In this regard, "VOC" refers to those organic compounds that contain less than 12 carbon atoms or have a vapor pressure greater than about 0.1 mm of mercury. For example, the composition may have, as initially applied, a total VOC content of about 55% or less (e.g., in preferred hairsprays), about 16% or less (e.g., in preferred mousses), or about 6% or less (e.g., in preferred gels). The VOC may be based on actual VOC content, or the VOC which is delivered upon initial dispensing from a package.

The carrier may also comprise conventional components such as are known in the art suitable for a given product form.

Optional Components

The present compositions can contain a wide variety of other optional ingredients that are suitable for application to human hair, including among them any of the types of ingredients known in the art for use in hair care compositions, especially hair setting compositions like hair spray compositions, mousses, gels and tonics. Generally, such other adjuvants collectively comprise from about 0.05% to about 20% by weight, preferably from about 0.1% to about 10%, more preferably 0.05% to about 5% by weight of the compositions. Such conventional optional adjuvants are well known to those skilled in the art and include, but are not limited to, plasticizers, surfactants (which may be anionic, cationic, amphoteric or nonionic), neutralizing agents, propellants, hair conditioning agents (e.g., silicone fluids, fatty esters, fatty alcohols, long chain hydrocarbons, isobutene, cationic surfactants, etc.), emollients, lubricants and penetrants such as various lanolin compounds, vitamins, proteins, preservatives, dyes, tints, bleaches, reducing agents and other colorants, sunscreens, thickening agents (e.g., polymeric thickeners, such as xanthan gum), physiologically active compounds for treating the hair or skin (e.g., anti-dandruff actives, hair growth actives) and perfume.

Non-exclusive examples of certain types of optional components are provided below.

a) Surfactants

The hair styling compositions can contain one or more surfactants, e.g., for emulsifying hydrophobic components which may be present in the composition. Surfactants are preferred for use in mousse products. Generally, if used, such surfactants will be used at a total level of from about 0.01% to about 10%, preferably from about 0.01% to about 5% and more preferably from about 0.01% to about 3%, by weight of the composition. A wide variety of surfactants can be used, including anionic, cationic, amphoteric, and zwitterionic surfactants.

Anionic surfactants include, for example: alkyl and alkenyl sulfates; alkyl and alkenyl ethoxylated sulfates; (preferably having an average degree of ethoxylation of 1 to 10), succinamate surfactants, such as alkylsulfosuccinamates and dialkyl esters of sulfosuccinic acid; neutralized fatty acid esters of isethionic acid; and alkyl and alkenyl sulfonates, including, for example, olefin sulfonates and beta-alkoxy alkane sulfonates. Preferred are alkyl and alkenyl sulfates and alkyl and alkenyl ethoxylated sulfates such as the sodium and ammonium salts of $C_{12}$–$C_{18}$ sulfates and ethoxylated sulfates with a degree of ethoxylation of from 1 to about 6, preferably from 1 to about 4, e.g., lauryl sulfate and laureth (3.0) sulfate.

Amphoteric surfactants include those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378. Others include alkyl, preferably $C_6$–$C_{22}$ and most preferably $C_8$–$C_{12}$, amphoglycinates; alkyl, preferably $C_6$–$C_{22}$ and most preferably $C_8$–$C_{12}$, amphopropionates; and mixtures thereof.

Suitable zwitterionic surfactants for use in the present compositions can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

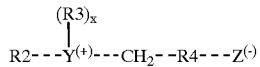

wherein R2 contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; x is 1 when Y is sulfur or phosphorus, 1 or 2 when Y is nitrogen; R4 is an alkylene or hydroxyalkylene of from 1 to about 4 carbon atoms and Z is a radical selected from the group consisting of carboxylate, sulfonate, sulfate, phosphonate, and phosphate groups. Classes of zwitterionics include alkyl amino sulfonates, alkyl betaines, and alkyl amido betaines.

Cationic surfactants useful in compositions of the present invention contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

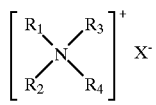

wherein $R_1$ is an aliphatic group of from 1 to 22 carbon atoms, or an aromatic, aryl or alkylaryl group having from 12 to 22 carbon atoms; $R_2$ is an aliphatic group having from 1 to 22 carbon atoms; $R_3$ and $R_4$ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups. Other quaternary ammonium salts useful herein are diquaternary ammonium salts.

Salts of primary, secondary and tertiary fatty amines are also suitable cationic surfactants for use herein. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidyl-behenylamine. Cationic amine surfactants included among those useful in the present invention are disclosed in U.S. Pat. No. 4,275,055, Nachtigal, et al., issued Jun. 23, 1981 (incorporated by reference herein).

Suitable cationic surfactant salts include the halogen, acetate, phosphate, nitrate, citrate, lactate and alkyl sulfate salts.

Nonionic surfactants include polyethylene oxide condensates of alkyl phenols (preferably $C_6$–$C_{12}$ alkyl, with a degree of ethoxylation of about 1 to about 6), condensation products of ethylene oxide with the reaction product of propylene oxide and ethylene diamine, condensation products of aliphatic alcohols with ethylene oxide, long chain (i.e., typically $C_{12}$–$C_{22}$) tertiary amine oxides, long chain tertiary phosphine oxides, dialkyl sulfoxides containing one long chain alkyl or hydroxy alkyl radical and one short chain (preferably $C_1$–$C_3$) radical, silicone copolyols, and $C_1$–$C_4$ alkanol amides of acids having a $C_8$–$C_{22}$ acyl moiety. Preferred nonionic surfactants are $C_1$–$C_4$ alkanol amides of acids having a $C_8$–$C_{22}$ acyl moiety, polyoxyethylene glycol stearyl ethers, and mixtures thereof. Specific examples which are preferred are Lauramide DEA, Steareth-21, Steareth-2, and Na Cocoyl Isethionate.

Additional surfactants suitable for use herein include those described in reference to the microemulsion.

b) Neutralizing Agents

Hair styling polymers which have acidic functionalities, such as carboxyl groups, are preferably used in at least partially neutralized form to promote solubility/dispersibility of the polymer. In addition, use of the neutralized form aids in the ability of the dried hair styling compositions to be removed from the hair by shampooing. The degree of neutralization must balance shampoo removability versus humidity resistance. Neutralization levels in excess of what is required for shampoo removability will result in excessively sticky products that will not hold as well in high humidity. When available acidic monomers are neutralized, it is preferred that from about 5% to 60%, more preferably from about 10% to about 40%, and even more preferably from about 12% to about 30% of the polymer (on a total polymer weight basis) be neutralized. The optimal level of neutralization for a specific polymer will depend on the polarity of the monomers selected, the specific ratios of the monomers to each other, and the percentage of acidic monomers. The level of base needed to neutralize the acid groups in a polymer for a specific % neutralization of the polymer may be calculated from the following equation:

$$\% \text{ Base in} = A \times (B/100) \times (C/D) \text{ composition}$$

A=% Polymer in composition
B=% of polymer to be neutralized (assuming acid groups are available)
C=MW of Base
D=MW of Acid monomer Any conventionally used base, including organic or inorganic (metallic or other) bases, can be used for neutralization of the polymers. Metallic bases are particularly useful in the present compositions. Hydroxides, where the cation is ammonium, an alkali metal or an alkaline earth metal, are suitable neutralizers for use in the present compositions. Preferred inorganic neutralizing agents for use in the compositions of the present invention are potassium hydroxide and sodium hydroxide. Examples of other suitable neutralizing agents which may be included in the hair styling compositions of the present invention include amines, especially amino alcohols such as 2-amino-2-methyl-1,3-propanediol (AMPD), 2-amino-2-ethyl-1,3-propanediol (AEPD), 2-mino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), triisopropanolamine (TIPA), dimethyl laurylamine (DML), dimethyl myristalamine (DMM) and dimethyl stearamine (DMS).

Polymers having basic functionalities, e.g., amino groups, are preferably at least partially neutralized with an acid, e.g., hydrochloric acid.

Neutralization can be accomplished by techniques well known in the art, and before or after polymerization of the monomers comprising the hair styling polymer.

c) Hair Conditioning Polymers

The compositions of the invention may include a hair conditioning polymer for purposes of improved wet combing, dry combing and/or improved manageability (e.g., frizz or static control). Hair conditioning polymers are typically used at a level of from about 0.001% to about 6%, more preferably from about 0.01% to about 5% of the composition.

Cationic and zwitterionic hair conditioning polymers are preferred. Suitable hair conditioning polymers include cationic polymers having a weight average molecular weight of from about 5,000 to about 10 million, and will generally have cationic nitrogen-containing moieties such as quaternary ammonium or cationic amino moieties, and mixtures thereof. Cationic charge density should be at least about 0.1 meq/gram, preferably less than about 3.0 meq/gram, which can be determined according to the well known Kjeldahl Method. Those skilled in the art will recognize that the charge density of amino-containing polymers can vary depending upon pH and the isoelectric point of the amino groups. The charge density should be within the above limits at the pH of intended use. Any anionic counterions can be utilized for the cationic polymers so long as they are compatible.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in *International Cosmetic Ingredient Dictionary*, Sixth Edition, 1995, which is incorporated by reference herein in its entirety.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of poly-vinyl acetate), maleic anhydride, propylene glycol, and ethylene glycol. The cationic polymers are described in detail in U.S. Pat. No. 4,733,677 which is hereby incorporated by reference to further describe the cationic polymers used for conditioning purposes.

The cationic amines can be primary, secondary, or tertiary amines, depending upon the particular species and the pH of the composition. In general, secondary and tertiary amines, especially tertiary amines, are preferred. The cationic polymers can comprise mixtures of monomer units derived from amine- and/or quaternary ammonium-substituted monomer and/or compatible spacer monomers.

Other cationic polymers that can be used include polysaccharide polymers, such as cationic cellulose derivatives, cationic starch derivative, and cationic guar gum derivatives. Other materials include quaternary nitrogen-containing cellulose ethers as described in U.S. Pat. No. 3,962,418, and copolymers of etherified cellulose and starch as described in U.S. Pat. No. 3,958,581, which descriptions are incorporated herein by reference.

Where the composition comprises a neutralized, anionic hair styling polymer and a zwitterionic hair conditioning polymer, the pH of the zwitterion is preferably adjusted to that of the neutralized hair styling polymer prior to combination therewith. Neutralization may be achieved by conventional methods using pH-adjusting agents such as are known in the art.

d) Propellants

When the hair styling compositions are to be dispensed from a pressurized aerosol container (e.g., certain hair sprays and mousses), a propellant which consists of one or more of the conventionally-known aerosol propellants can be used to propel the compositions. A suitable propellant for use can be any gas conventionally used for aerosol containers, preferably a liquifiable gas. Suitable propellants for use are volatile hydrocarbon propellants which can include liquified lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, nitrogen, carbon dioxide, nitrous oxide, and atmospheric gas. For hair sprays and mousses, the selection of appropriate hydrocarbons is made to provide a stable system giving the desired spray/foam quality.

The aerosol propellant may be mixed with the present hair styling compositions and the amount of propellant to be mixed is governed by normal factors well known in the aerosol art. Generally, for liquifiable propellants, the level of propellant is from about 1% to about 60% by weight of the total composition. For hair sprays, the propellant level is from about 10% to about 60% by weight of the total composition, preferably from about 15% to about 50% by weight of the total composition. For mousses, the level of propellant is generally from about 1% to about 30% and more preferably from about 4% to about 15% by weight of the total composition.

Alternatively, pressurized aerosol dispensers can be used where the propellant is separated from contact with the hair styling composition such as a two compartment can of the type sold under the tradename SEPRO from American National Can Corp.

Other suitable aerosol dispensers are those characterized by the propellant being compressed air which can be filled into the dispenser by means of a pump or equivalent device prior to use. Such dispensers are described in U.S. Pat. No. 4,077,441, Mar. 7, 1978, Olofsson and U.S. Pat. No. 4,850, 577, Jul. 25, 1989, TerStege, both incorporated by reference herein, and in U.S. Ser. No. 07/839,648, Gosselin et al., filed Feb. 21, 1992 now abandoned, also incorporated by reference herein. Compressed air aerosol containers suitable for use herein are also those previously marketed by The Procter & Gamble Company under their tradename VIDAL SASSOON AIRSPRAY® hair sprays.

Furthermore, non-aerosol foams may also be mixed with the present hair styling composition such that the final composition is dispensable as a stable foam. A composition is "dispensable as a stable foam" when it produces a foam when dispensed from a package or container which is either pressurized or equipped with an air or gas mixing device like the F2 non-aerosol foamer described in U.S. Pat. Nos 5,271,530; 5,337,929; and 5,443,569; all of which are herein incorporated by reference.

e) Silicone Polyether Surfactant

Compositions of the present invention may contain a silicone polyether suitable for stabilizing the organopolysiloxane microemulsion. The silicone polyether is especially preferred for relatively high alcohol compositions (e.g., at least about 40% monohydric alcohol). The silicone polyether comprises a polymeric portion comprising repeating organosiloxane units, and a polymeric portion comprising repeating alkylene oxide units (i.e., a silicone-polyoxyalkylene copolymer). Suitable silicone polyethers are those which are surface active in the carrier employed in the compositions of the invention. As will be understood in the art, the surface activity of the silicone polyether will depend on the molecular weight of the polymeric portion comprising repeating organosiloxane units. This portion should be of sufficiently large molecular weight such that it is insoluble in the carrier, yet not so large that it renders the whole molecule insoluble in the carrier. When used, the silicone polyether is used in an amount effective to stabilize the microemulsion, preferably from about 0.02% to about 7%, more preferably about 0.05% to about 5%, of the total composition.

The silicone polyether may be a silicone—linear polyoxyalkylene block copolymer (wherein the polymeric backbone comprises silicone blocks and polyoxyalkylene blocks, optionally having grafts), a silicone—graft polyoxyalkylene copolymer (wherein the polymeric backbone comprises silicone blocks and the polyoxyalkylene blocks are present as grafts rather than in the backbone), or a mixture thereof. Linear copolymers are preferred.

Silicone linear block polyethers, particularly preferred for relatively high alcohol compositions (e.g., at least about 40% monohydric alcohol) include those having the formula (I):

wherein

M' is a monofunctional unit $R_2R'SiO_{1/2}$;

D is a difunctional unit $R_2SiO_{2/2}$;

D' is a difunctional unit $RR'SiO_{2/2}$;

R is independently H, $C_1$–$C_6$ alkyl, or aryl, preferably H or $C_1$–$C_4$ alkyl, more preferably $CH_3$;

R' is independently, an oxyalkylene containing moiety, H, or $CH_3$;

b is an integer of from about 10 to about 1000, preferably about 10 to about 500, more preferably about 20 to about 200; and c is an integer of from 0 to about 100, preferably 0 to about 50, more preferably c is 0, provided that when c is 0, at least one M' contains an oxyalkylene moiety.

Preferred R' in structure (I) are those having the formula:

wherein

R" is a divalent radical for connecting the oxyalkylene portion of moiety R' to the siloxane backbone, preferably —$(C_mH_{2m})$—, wherein m is an integer of from 2 to 8, preferably from 2–6, more preferably from 3–6;

R''' is a terminating radical for the oxyalkylene portion of the moiety R', e.g., H, hydroxyl, $C_1$–$C_6$ alkyl, aryl, alkoxy (e.g., $C_1$–$C_6$) or acyloxy (e.g., $C_1$–$C_6$), preferably hydroxyl;

n is an integer of from 2 to 4, preferably 2 to 3 (i.e., the oxyalkylene group may contain ethylene oxide, propylene oxide and/or butylene oxide units); and y is 1 or greater, wherein the total y from all the oxyalkylene units in the copolymer is 10 or greater.

The oxyalkylene moiety of R' may be a random copolymer, a block copolymer or a mixture thereof. Preferred R' groups in structure (I) are those wherein the oxyalkylene units are selected from ethylene oxide units (EO), propylene oxide units (PO), and mixtures thereof. More preferred are those wherein the oxyalkylene units have an ethylene oxide unit (EO) to propylene oxide unit (PO) ratio of $EO_{10-100}PO_{0-100}$, more preferably $EO_{20-70}PO_{20-70}$, most preferably $EO_{30-70}PO_{30-70}$, based on the total oxyalkylene in the silicone polyether.

Particularly preferred silicone polyethers for relatively high alcohol compositions (e.g., at least about 40% monohydric alcohol) are those having the formula:

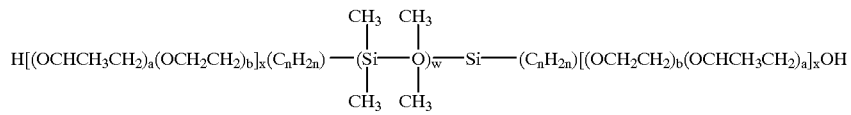

wherein n is as defined above, x is independently an integer of 1 or greater, a and b independently are an integer of from about 15 to about 30, and w is an integer of from about 20 to about 200, preferably from about 30 to about 200. Such silicone polyethers are commercially available from Goldschmidt Chemical Company under the tradename TEGO-PREN 5830.

Preferred silicone graft polyethers for use herein are those having the formula (II):

$$MD_bD'_cM$$

wherein:

M is a monofunctional unit $R_3SiO_{1/2}$,

D is a difunctional unit $R_2SiO_{2/2}$,

D' is a difunctional unit $RR'SiO_{2/2}$,

R is independently H, $C_1$–$C_6$ alkyl, or aryl, preferably H or $C_1$–$C_4$ alkyl, more preferably $CH_3$, R' is an oxyalkylene containing moiety, b is an integer of from about 10 to about 1000, preferably about 100 to about 500, and c is an integer of from 1 to about 100, preferably 1 to about 50.

Preferred R' are those having the formula

wherein

R" is a divalent radical for connecting the oxyalkylene portion of moiety R' to the siloxane backbone, preferably —$(C_mH_{2m})$—, wherein m is an integer of from 2 to 8, preferably 2–6, more preferably 3–6;

R''' is a terminating radical for the oxyalkylene portion of moiety R', e.g., H, hydroxyl, $C_1$–$C_6$ alkyl, aryl, alkoxy (e.g., $C_1$–$C_6$) or acyloxy (e.g., $C_1$–$C_6$), preferably hydroxy or acyloxy, more preferably hydroxyl;

n is an integer of from 2 to 4, preferably 2 to 3 (i.e., the oxyalkylene group may contain ethylene oxide, propylene oxide and/or butylene oxide units); and y is 1 or greater.

The oxyalkylene moiety of R' may be a random copolymer, a block copolymer or a mixture thereof. Preferred R' groups are those wherein the oxyalkylene units are selected from ethylene oxide units (EO), propylene oxide units (PO), and mixtures thereof. More preferred are those wherein the oxyalkylene units have an ethylene oxide unit (EO) to propylene oxide unit (PO) ratio of $EO_{10-100}PO_{0-100}$, more preferably $EO_{10-30}PO_{1-30}$, based on the total oxyalkylene in the silicone polyether.

In this regard, Table 1 shows some representative silicone graft polyethers:

TABLE 1

| Silicone Polyether* | Structure | Weight % EO | Weight % PO | HLB** |
|---|---|---|---|---|
| A | EO | 19 | 0 | 6.8 |
| B | EO | 40 | 0 | 8.0 |
| C | EO/PO | 34 | 0.4 | 6.8 |
| D | EO/PO | 41 | 12 | 8.2 |
| E | EO/PO | 34 | 39 | 5.0 |
| F | EO/PO | 32 | 42 | 6.4 |
| G | EO/PO | 30 | 40 | 5.7 |

*Silicone Polyethers A and B contain less than 20 D units and less than 5 D' units. Silicone Polyethers C–G contain from 100–200 D units and 10–30 D' units.
**Hydrophilic lipophilic balance (HLB) is determined by calculating the weight percent of EO and dividing this value by five.

Silicone polyethers of this type are further described in the above referenced patent application Ser. No. 08/929,721 now U.S. Pat. 5,891,954.

Siloxane-oxyalkylene copolymers, i.e., silicone polyethers, can be prepared according to methods generally described in the standard text on silicone chemistry entitled "Chemistry and Technology of Silicones," by Walter Noll, Academic Press Inc., Orlando, Fla., (1968), on pages 373–376. Silicone polyethers are also available from a number of commercial sources such as:

| Trade Name | Supplier | Silicone Content % | EO and/or PO | Molecular Weight |
|---|---|---|---|---|
| D.C.Q2-5220 | Dow Corning[1] | 14 | EO & PO | 3102 |
| D.C.193 | " | 33 | EO | — |
| D.C.190 | " | 24 | EO & PO | 2570 |
| D.C. Q4-3667 | " | 37 | EO | 2400 |
| Silwet L-7200 | OSI[2] | 31 | EO & PO | 19,000 |

-continued

| Trade Name | Supplier | Silicone Content % | EO and/or PO | Molecular Weight |
|---|---|---|---|---|
| Tegopren 5830/ Abil B8830 | Goldschmidt A.G.[3] | 55 | 40% EO/60% PO | 7800 |
| Tegopren 5830-A | Goldschmidt A.G.[3] | 50 | 30% EO/70% PO | 9000 |
| Tegopren 5830-B | Goldschmidt A.G.[3] | 50 | 60% EO/40% PO | 9000 |
| Abil B8851 | Goldschmidt A.G.[3] | — | EO & PO | >1400 |
| Abil B8863 | Goldschmidt A.G.[3] | — | EO & PO | >3000 |
| Abil EM 97 neat | Goldschmidt A.G.[3] | 75 | 60% EO/40% PO | 14,000–15,000 |

[1]Dow Corning of Midland, Michigan
[2]OSI Specialties of Lisle, Il.
[3]Hopewell, VA Other silicone polyethers are available as SF-1188 offered by General Electric of Waterford, N.Y., and KF353A offered by Shin Etsu Silicones of America of Torrance, Calif. Additional silicone polyethers are described in U.S. Pat. No. 4,871,529, incorporated herein by reference.

f) Other Optional Components

Compositions of the invention may contain a variety of other ingredients such as are conventionally used in a given product form. The compositions hereof may, for example, be in the form of a hairspray, mousse, gel, lotion, cream, pomade, spray-on product such as spray-on gel, heat protectant spray, volumizing spray, spritz, hair tonic, and the like. The compositions may be aerosol or non-aerosol. Such compositions are described, for example in California Code of Regulations, Regulation for Reducing Volatile Organic Compound Emissions from Consumer Products, Amendment 2, Consumer Products, Sections 94507–94717, Title 17, filed Sep. 19, 1991 and effective Oct. 21, 1991; and in Formulation and Function of Cosmetics, J. S. Jellinek, Wiley Interscience (1970), each incorporated herein by reference.

Method of Making

The hair styling compositions of the present invention can be made using conventional formulation and mixing techniques. A liquid hydrophilic non-polymeric cationic compound containing at least one quaternary ammonium moiety, hair styling polymer and the solvent are mixed to provide a homogeneous mixture. Any other ingredients are then added and mixed to yield the final composition. If the polymer is neutralized, the neutralizer is preferably added prior to addition of other ingredients. For hair spray products, the composition is packaged in conventional mechanical pump spray devices, or alternatively, in the case of aerosol sprays products, the composition is packaged in conventional aerosol canisters along with an appropriate propellant system (also applicable for mousses). Other hair styling compositions including tonics, lotions, and gels, are typically packaged in a conventional bottle or tube.

When the compositions of the present invention comprise a silicone microemulsion, it is important to add the silicone microemulsions to the system when some water (or other polar material) is present. The water helps to maintain the stability of the silicone microemulsions in the composition. The amount of water which is preferably present depends on the type of hair styling polymer and the presence and type of silicone copolyol. If the composition does not contain a silicone copolyol, at least about 30% water is preferably present. Where the composition contains a silicone copolyol having structure (1) (e.g., Tegopren), at least about 3% water is preferably present. When the composition contains other dimethicone copolyols at least about 25% water is preferably present.

Additionally, it is desirable to not impart high shear rates to the composition once the silicone microemulsion has been added, since shear might break the emulsion. Also, the silicone microemulsion is typically added after any thickeners or surfactants.

Method of Use

The compositions of the present invention are used in conventional ways to provide the hair care benefits of the present invention. Such methods generally involve application of an effective amount of the product to dry, slightly damp, or wet hair before and/or after the hair is dried and arranged to a desired style. Application of the product is normally effected by spraying or atomizing the product using an appropriate device, e.g. a mechanical pump spray, a pressurized aerosol container, or other appropriate means. Other hair styling compositions including tonics, lotions, and gels, are typically dispensed from a conventional bottle or tube, and applied directly to the hair or first dispensed to the hand and then to the hair. The composition is then dried or allowed to dry. By "effective amount" is meant an amount sufficient to provide the hair hold and style benefits desired. In general, from about 0.5 g to about 30 g of product is applied to the hair, depending upon the particular product formulation, dispenser type, length of hair, and type of hair style.

The present compositions are also useful in other applications where the benefits of the composition hereof may be realized. For example, other applications in the personal care area or household care area may benefit from a composition containing a polymer having hair styling properties, along with the silicone microemulsion.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or INCI name or CTFA name.

Examples I–III

The following are mousse concentrate compositions representative of the present invention:

| | Examples: | | |
|---|---|---|---|
| | I | II | III |
| Component | Weight % (as added) | Weight % (as added) | Weight % (as added) |
| Water | 80.83 | 79.50 | 78.51 |
| PVP/VA Copolymer (50% active) [1] | 6.00 | 6.00 | 6.00 |
| Polyquaternium-4 [2] | 0.50 | — | 0.50 |
| Polyquaternium-4 [3] | — | 1.00 | — |
| Glycerine | 6.00 | 6.00 | 6.00 |
| Propylene Glycol | 1.00 | 1.00 | 1.00 |
| Chitosan Lactate [4] | 0.20 | 0.20 | 0.20 |
| Undeceth-9 [5] | 0.25 | 0.25 | 0.40 |
| Steareth 21 [6] | 0.20 | 0.20 | 0.20 |
| Preservatives | 0.92 | 0.92 | 0.92 |
| Perfume | 0.10 | 0.10 | 0.10 |
| Quaternium-22 (60% active) [7] | 2.00 | 3.33 | 4.17 |

-continued

| | Examples: | | |
|---|---|---|---|
| Component | I Weight % (as added) | II Weight % (as added) | III Weight % (as added) |
| Silicone Microemulsion (25% active) [8] | 2.00 | 1.50 | 2.00 |

[1] PVP/VA 735W, ISP
[2] Celquat H-100, National Starch
[3] Celquat L-200, National Starch
[4] Kytamer L, Amerchol
[5] Neodol 1–9, Shell
[6] BRIJ 721s, ICI
[7] Ceraphyl ® 60, ISP.
[8] DC 2-1281 - Dow Corning silicone microemulsion with a cationic surfactant system and with a particle size of 25 nm and an internal phase viscosity of 1,200 cps. (no dimethicone copolyol)

Method of Making for Examples I–III:

A premix is prepared by completely dissolving the Chitosan Lactate in approximately 30% of the available water. The premix is then milled until a uniform consistency is achieved.

The main mix is prepared by heating water to 130 F. Then, PVP/VA Copolymer and Polyquaternium-4 are dissolved in the remaining water with vigorous agitation. Then, with agitation, Neodol 1-9 and BRIJ 721S are dissolved in the mix. Next, Glycerine, Propylene Glycol, and Ceraphyl 60 are added. Then Disodium EDTA is slowly added with vigorous agitation until it is completely dissolved. Lastly, Phenoxyethanol, Benzyl Alcohol, and Silicone Microemulsion are added.

Hydrocarbon (A 46) propellant is then added to the concentrate at about a 7% level of the final can position relative to 93% of the above described concentrate formulas in an appropriate aluminum can with an appropriate aerosol valve.

Examples IV–VI

The following are mousse concentrate compositions representative of the present invention:

| | Examples: | | | |
|---|---|---|---|---|
| Component | IV Weight % (as added) | V Weight % (as added) | VI Weight % (as added) | VII Weight % (as added) |
| Water | 78.51 | 79.01 | 78.51 | 79.88 |
| Ethanol (200 proof) | | | | 10.00 |
| PVP/VA Copolymer (50% active) [1] | 6.00 | 6.00 | 6.00 | — |
| Polyquaternium-4 [2] | 0.50 | 0.50 | 0.50 | 0.50 |
| Polyquaternium-11 (20% active) [3] | | | | |
| Glycerine | 6.00 | 6.00 | 6.00 | 0.30 |
| Propylene Glycol | 1.00 | 1.00 | 1.00 | — |
| Chitosan Lactate [4] | 0.20 | 0.20 | 0.20 | — |
| Undeceth-9 [5] | 0.40 | 0.40 | 0.40 | — |
| Lauramide DEA [6] | — | — | — | 0.20 |
| Steareth 21 [7] | 0.20 | 0.20 | 0.20 | 0.10 |
| Preservatives | 0.92 | 0.92 | 0.92 | 0.92 |
| Perfume | 0.10 | 0.10 | 0.10 | 0.10 |
| Di-Lauryl Acetyl Dimonium Chloride [8] | 4.17 | — | — | — |
| Lauryl Methyl Gluceth-10 hydroxylpropyl Dimonium Chloride (25% active) [9] | — | 4.17 | — | — |
| PPG-9 Diethylmonium Chloride [10] | — | — | 4.17 | — |
| Quaternium-22 (60% active) [11] | | | | 5.00 |
| Silicone Microemulsion (25% active) [12] | 2.00 | 1.50 | 2.00 | — |
| Silicone Microemulsion (25% active) 13 | — | — | — | 3.00 |

[1] PVP/VA 735W, ISP
[2] Celquat H-100, National Starch
[3] Gafquat-755N, ISP
[4] Kytamer L, Amerchol
[5] Neodol 1–9, Shell
[6] Monamide 716, Mona
[7] BRIJ 721s, ICI
[8] Schercoquat ALA, Scher Chemicals
[9] Gluquat™ 125, Amerchol
[10] Emcol CC9, Witco
[11] Ceraphyl ® 60, ISP.
[12] DC 2-1281 - Dow Corning silicone microemulsion with a cationic surfactant system and with a particle size of 25 nm and an internal phase viscosity Of 1,200 cps. (no dimethicone copolyol)
[13] DC-2-5932 silicone microemulsion from Dow Corning with a particle size of 24 nm, a cationic surfactant system, and a silicone with an internal phase viscosity = 1,200 cps.

Examples IV–VI Method of Making:

A premix is prepared by completely dissolving the Chitosan Lactate in approximately 30% of the available water. The premix is then milled until a uniform consistency is achieved.

The main mix is prepared by heating water to 130 F. Then, PVP/VA Copolymer and Polyquaternium-4 are dissolved in the remaining water with vigorous agitation. Then, with agitation, Neodol 1-9 and BRIJ 721S are dissolved in the mix. Next, Glycerin, Propylene Glycol, and the quaternary compound are added. Then Disodium EDTA is slowly added with vigorous agitation until it is completely dissolved. Lastly, Phenoxyethanol, Benzyl Alcohol, and Silicone Microemulsion are added.

Hydrocarbon (A 46) propellant is then added to the concentrate at about a 7% level of the final can composition relative to 93% of the above described concentrate formulas in an appropriate aluminum can with an appropriate aerosol valve.

Example VII Making Method:

The first premix is prepared by adding the ethanol to ½ of the water (save remaining ½ for premixing Silicone Microemulsion, preservatives and surfactants). Next, add the Celquat H-100 and mix until uniformly dissolved in ethanol/water. Add the Gafquat-755N and mix until uniformly dissolved. With vigorous agitation, add the perfume, the quaternary compound, and the glycerine.

The second premix is prepared by dissolving the surfactants (Lauramide DEA, Steareth 21) in the remaining water with heat (120° F.) and agitation. Remove the mix from heat when the surfactants are completely dissolved.

Next, add the preservatives and the silicone microemulsion to the mix with vigorous agitation.

The final concentrate step involves combining the first and second premixes under vigorous agitation and placing the concentrate in a suitable aluminum can at 7% of total fill with an appropriate mousse valve. The valve is crimped to the can and a vacuum is applied to deaerate. The can is then pressurized with propellant.

| Can Composition: | Weight % |
|---|---|
| Concentrate Composition (above) | 93.00 |
| Hydrofluorocarbon 152A (propellant) | 4.76 |
| Isobutane (A31 propellant) | 2.24 |

Examples IX–XI

The following are gel compositions representative of the present invention:

| | Examples | | |
|---|---|---|---|
| Component | IX Weight % | X Weight % | XI Weight % |
| Water | 80.03 | 74.75 | 81.55 |
| Ethanol | 5.00 | 16.00 | — |
| PVP [1] | — | — | 2.00 |
| PVP/VA Copolymer (50% active) [2] | 6.00 | — | 3.00 |
| Polyquaternium-16 [3] | — | 2.00 | — |
| Polyquaternium-47 [4] | — | — | 0.50 |
| Benzophenone-4 [5] | — | 0.10 | — |
| Isosteareth 20 [6] | 0.30 | — | 0.30 |
| Perfume | 0.20 | 0.20 | 0.20 |
| Diethylene Glycol [7] | 0.30 | — | — |
| Propylene Glycol | — | — | 0.20 |
| Triethanolamine [8] | 0.47 | — | — |
| Glycerine | 0.25 | — | 0.25 |
| Carbomer [9] | 0.50 | — | — |
| Hydroxypropyl Guar [10] | — | 1.00 | — |
| Hydroxyethyl Cellulose [11] | — | — | 1.00 |
| Isostearamidopropyl Ethyldimonium Ethosulfate [12] | 4.00 | — | — |
| PPG-40 Diethylmonium Chloride [13] | — | — | 6.00 |
| Quaternium-22 (60% active) [14] | — | 2.00 | — |
| Silicone Microemulsion (25% active) [15] | 2.00 | — | — |
| Silicone Microemulsion (37% active) [16] | — | 3.00 | — |
| Silicone Microemulsion (25% active) [17] | — | — | 2.00 |
| Preservatives | 0.95 | 0.95 | — |

[1] PVP K-30, ISP
[2] PVP/VA 735W, ISP
[3] Luviquat FC 550, BASF
[4] Merquat - 2001, Calgon.
[5] Uvinul MS-40, BASF
[6] Arosurf 66 E-20, Witco
[7] Diethylene glycol, Ashland
[8] Triethanol amine, Dow Chemical
[9] Carbopol 940, BF Goodrich
[10] Jaguar HP-105, Rhone-Poulenc
[11] Cellosize PCG-10, Amerchol
[12] Schercoquat IAS, Scher Chemicals
[13] Emcol CC42, Witco
[14] Ceraphyl ® 60, ISP.
[15] DC-1845 - Silicone microemulsion from Dow Corning with a particle size of 33 nm, an anionic/nonionic surfactant system, and a silicone with an internal phase viscosity = 70,000 cps.
[16] DC-2-5932 silicone microemulsion from Dow Corning with a particle size of 24 nm, a cationic surfactant system, and a silicone with an internal phase visocosity = 1,200 cps.
[17] DC-1550 silicone microemulsion from Dow Corning with a particle size of 50 nm, an anionic/nonionic surfactant system, and a silicone with an internal phase viscosity = 100,000 cps.

Method of Making for Example IX:

A premix is prepared by completely dissolving the PVP/VA Copolymer in 30% of the batch water (100° F.) with vigorous agitation. In the following order, under continued agitation, add the Diethylene glycol, the Isosteareth-20, the perfume, the Glycerin, the ethanol, the quaternary compound and the preservatives.

The final mix is prepared under vigorous agitation by dissolving the Carbomer in 50% of the batch water (120° F.) until the carbomer is fully hydrated. With mild agitation, add Triethanol amine to carbomer/water, allowing gelation to occur. With continued mild agitation, add the premix and the silicone microemulsion (premixed with the remaining water) to the mix.

Making Method for Example X:

A premix is prepared by adding the Polyquaternium-16 to 60% of the water under moderate agitation. Next with vigorous agitation, add the Benzophenone, the Ethanol, the Perfume, the quaternary compound, and the preservatives.

The final mix is prepared by adding the Hydroxypropyl Guar to 30% of the water, mixing vigorously until the guar hydrates completely. Next, add the premix with gentle agitation. Then add the silicone microemulsion (premixed with the remaining water) to the mix with mild agitation.

Making method for Example XI:

The premix is prepared by completely dissolving the PVP and PVP/VA Copolymer in 30% of the batch water (120° F.) with vigorous agitation. Under continued agitation, add the Isosteareth-20 and the perfume, and then remove the mix from the heat. While still vigorously agitating, add the Glycerin, the Merquat 2001, the quaternary compound, and the preservatives.

The final mix is prepared under vigorous agitation by dissolving the HEC in 50% of the batch water (155° F.) until the HEC is fully hydrated. With mild agitation, add premix and then the silicone microemulsion (premixed with the remaining water).

Example XII

The following is a non-aerosol mousse composition representative of the present invention:

| Component | Weight % |
|---|---|
| Water | 84.04 |
| PVP/VA Copolymer (50% active) [1] | 3.00 |
| PVP/Dimethylaminoethylmethacrylate Copolymer (20% active) [2] | 2.50 |
| Sodium Cocoyl Isethionate [3] | 0.75 |
| Isosteareth-10 [4] | 0.10 |
| Perfume | 0.10 |
| Preservatives | 0.91 |
| Quaternium-22 (60% active) [5] | 6.60 |
| Silicone Microemulsion (25% active) [6] | 2.00 |

[1] PVP/VA 735W, ISP
[2] Copolymer 845, ISP
[3] Aerosurf 66E10, Witco
[4] Tauranol I-78, Finetex
[5] Ceraphyl ® 60, ISP.
[6] DC 2-1281 - Dow Corning silicone microemulsion with a cationic surfactant system and with a particle size of 25 nm and an internal phase viscosity Of 1,200 cps. (no dimethicone copolyol)

The first premix is prepared by adding both polymers PVP/VA Copolymer and Copolymer 845 to half of the water with agitation and then add the quaternary compound and the preservatives.

The second premix is prepared by adding the Sodium Cocoyl Isethionate to 40% of the water (heat and vigorous agitation may be required). Combine the Isosteareth-10 and perfume and add to the mix with agitation. Next, add the silicone microemulsion, premixed with the remaining (10%) of the water with agitation.

The final concentrate step involves combining the first and second premixes.

Example XIII

The following is a Sculpting Spray representative of the present invention:

| Concentrate composition: | |
|---|---|
| Component | Weight % |
| Ethanol (200 proof) | 51.50 |
| Butyl Ester of PVM/MA copolymer (50% active in ethanol) [1] | 12.00 |
| Perfume | 0.10 |
| Water | 32.64 |
| Aminomethyl propanol [2] | 0.26 |
| PEG-2 Cocomonium Chloride [3] | 0.50 |
| Silicone Microemulsion (25% active) [4] | 3.00 |

[1] Omnirez-2000, ISP
[2] AMP-95, Angus
[3] Variquat K 638, Witco
[4] DC-1845 - Silicone microemulsion from Dow Corning with a particle size of 33 nm, an anionic/nonionic surfactant system, and a silicone with an internal phase viscosity = 77,000 cps.

This product is prepared by combining the alcohol and water (95% of the water). Begin agitation and add the neutralizer (Aminomethyl propanol). Next, add the Omnirez-2000 and mix until completely dissolved. Then add the fragrance with agitation. Add the silicone microemulsion premixed with the remaining water. Lastly add the quaternary compound.

Example XIV

The following is a spray gel composition representative of the present invention:

| Component | Weight % |
|---|---|
| Ethanol | 38.00 |
| PVP/VA Copolymer (50% active) [1] | 6.00 |
| Polyquaternium-11 [2] | 0.50 |
| Isosteareth 20 [3] | 0.30 |
| Perfume | 0.20 |
| Diethylene Glycol [4] | 0.30 |
| Water | 47.50 |
| Glycerin | 0.25 |
| PEG-15 Cocomonium Chloride [5] | 2.00 |
| Silicone Microemulsion (25% active) [6] | 2.00 |
| Preservatives | 0.95 |

[1] PVP/VA 735W, ISP
[2] Gafquat - 755N, ISP
[3] Arosurf 66 E-20, Witco
[4] Diethylene glycol, Ashland
[5] Variquat K1215
[6] DC 2-1281 - Dow Corning Silicone microemulsion with a particle size of 30 nm, and an internal phase viscosity of 1,500.

This concentrate is prepared by completely dissolving the Polyquaternium-11 and PVP/VA Copolymer in the ethanol and the batch water with vigorous agitation. Under continued vigorous agitation, add the Diethylene glycol, the Isosteareth-20, the perfume, the Glycerin, and preservatives. Next, add the silicone microemulsion to the mix with mild agitation.

Example XV

The following is a Non-Aerosol Hairspray composition representative of the present invention:

| Component | Weight % |
|---|---|
| Ethanol (200 proof) | 55.00 |
| Acrylate Copolymer [1] | 4.00 |
| Dimethyl myristalamine | 0.10 |
| Isododecane [2] | 0.50 |
| Perfume | 0.10 |
| Diisobutyl Adipate [3] | 0.10 |
| Sodium Hydroxide Solution (30% active) | 1.29 |
| Water | 33.91 |
| Quaternium-22 (60% active) [4] | 1.00 |
| Silicone Microemulsion (25% active) [5] | 4.00 |

[1] 75/25 Tertbutylacrylate/Acrylic Acid/, polymer molecular weight = 80,000
[2] Permethyl 99A, Presperse Inc.
[3] Plasthall DIBA, C. P. Hall
[4] Ceraphyl ® 60, ISP.
[5] DC-2-5791 - Silicone microemulsion from Dow Corning with a particle size of 49 nm, an anionic/nonionic surfactant system, and a silicone with an internal phase visocosity = 77,000.

This product is prepared by completely dissolving the Acrylate Copolymer in ethanol with vigorous agitation (there should be no visible white flakes). Under continued vigorous agitation, add the dimethyl myristal amine, the Isododecane, the perfume, and the DIBA. While still agitating, slowly add the NaOH. It is important to achieve a complete neutralization reaction. Then add the water and mix until a uniform mixture results. Add the silicone microemulsion to the mix with agitation and finally add the quaternary compound.

Example XVI

The following is an Aerosol Hairspray composition representative of the present invention:

| Component | Weight % |
|---|---|
| Ethanol (200 proof) | 40.0 |
| Methacrylate Copolymer (50% active) [1] | 5.0 |
| Perfume | 0.10 |
| Cyclomethicone | 0.30 |
| Aminomethyl propanol (AMP) | 0.70 |
| Water | 24.50 |
| Di-Lauryl Acetyl Dimonium Chloride [2] | 0.22 |
| Silicone Microemulsion (25% active) [3] | 1.00 |
| Corrosion Inhibitors | 0.18 |
| Dimethyl Ether (propellant) | 14.00 |
| Isobutane (propellant) | 14.00 |

[1] Balance CR, National Starch
[2] Schercoquat ALA. Scher Chemicals
[3] DC-1845 - Silicone microemulsion from Dow Corning with a particle size of 33 nm, an anionic/nonionic surfactant system, and a silicone with an internal phase viscosity = 70,000 cps.

This concentrate is prepared by adding the AMP to the ethanol with agitation. Adding the methacrylate copolymer to the mix with agitation. Next, add the cyclomethicone and perfume to the mix with agitation. Then, add the corrosion inhibitors to the water and add the water to the batch. The batch concentrate is put into a suitable container, with a suitable valve and is pressurized with the propellants.

Examples XVII & XVIII

The following is a spray conditioner composition and a hair tonic representative of the present invention:

|  | Example | |
|---|---|---|
| Component | XVII Weight % | XVIII Weight % |
| Water | 90.31 | 82.38 |
| PVP/VA Copolymer (50% active) [1] | 1.00 | 1.00 |
| Polyquaterium-11 [2] | — | 0.50 |
| Polyquaterium-37 [3] | 1.00 | — |
| Propylene Glycol Dicaprylate/Diccaprate [3] | (total % of 3 | — |
| PPG-1 Trideceth-6 [3] | components) | — |
| PEG-4 [4] | 0.45 | — |
| PEG 5M [5] | 0.01 | — |
| Octyl Methoxycinnamate [6] | 0.01 | — |
| Preservatives | 0.52 | 0.52 |
| Dimethicone [7] | 0.42 | — |
| Glycerine | — | 6.00 |
| Propylene Glycol | — | 0.5 |
| Perfume | 0.11 | 0.10 |
| Quaterium-22 (60% active) [8] | 4.17 | 6.00 |
| Silicone Microemulsion (25% active) [9] | 2.00 | 3.00 |

[1] PVP/VA 735W, ISP
[2] Gafquat 755, ISP
[3] Salcare SC96, Allied Colloids
[4] Carbowax PEG 200, Union Carbide
[5] Polyox WSR N-80, Amerchol
[6] Escalol 557, ISP
[7] GE Tween Emulsion CM2233, G.E.
[8] Ceraphyl ® 60, ISP.
[9] DC 2-1281 - Dow Corning silicone microemulsion with a cationic surfactant system and with a particle size of 25 nm and an internal phase viscosity Of 1,200 cps. (no dimethicone copolyol)

Method of Making for Examples XVII & XVIII:

Combine ingredients listed above one at a time with vigorous agitation in order listed.

What is claimed is:

1. A personal care composition suitable for styling hair, comprising:
   (a) from about 0.01% to about 20% of a non-silicone containing polymer suitable for hair styling;
   (b) an organopolysiloxane microemulsion comprising:
      (i) an organopolysiloxane dispersed as particles in the microemulsion, wherein the organopolysiloxane is substantially free of amino groups in combination with hydroxyl groups and has an average particle size of less than about 80 nanometers, and
      (ii) a surfactant system for dispersing the organopolysiloxane in the microemulsion, which is compatible with the non-silicone containing polymer;
   wherein the amount of microemulsion is such that the personal care composition comprises from about 0.01% to about 10% of the organopolysiloxane; and
   (c) from about 0.1% to about 20% of a liquid hydrophilic non-polymeric cationic compound containing at least one quaternary ammonium moiety; and
   (d) a carrier comprising:
      (i) from about 3% to about 99%, by weight of the composition, of a first solvent selected from the group consisting of water; water soluble organic solvents; organic solvents which are strongly to moderately strong in hydrogen-bonding parameter; and mixtures thereof; wherein the first solvent is other than $C_1$–$C_3$ monohydric alcohol, $C_1$–$C_3$ ketone and $C_1$–$C_3$ ether, and
      (ii) optionally, from about 0% to about 55% of a second solvent selected from the group consisting of $C_1$–$C_3$ monohydric alcohols, $C_1$–$C_3$ ketones, $C_1$–$C_3$ ethers, and mixtures thereof.

2. The composition of claim 1 wherein said composition comprises from about 0.1% to about 10% of said cationic compound.

3. The composition of claim 1 wherein said cationic compound further comprises at least one glycosyl moiety.

4. The composition in claim 3 wherein said cationic compound is selected from the group consisting of lauryl methyl gluceth-10-hydroxylpropyl dimonium chloride, and mixtures thereof.

5. The composition in claim 3 wherein said cationic compound is Quaternium-22.

6. The composition of claim 1 wherein said cationic compound further comprises at least one alkylene oxide moiety.

7. The composition of claim 6 wherein said cationic compound is selected from the group consisting of PPG-40 diethylmonium chloride, PEG-15 cocomonium chloride, PEG-2 cocomonium chloride, PPG-9 diethylmonium chloride, PPG-40 diethylmonium chloride, and mixtures thereof.

8. The composition of claim 1 wherein said cationic compound further comprises at least one ethyl sulfate moiety.

9. The composition of claim 8 wherein said cationic compound is selected from the group consisting of coamidopropyl ethyldimonium ethosulfate, stearamidopropyl ethyldimonium ethosulfate, isostearamidopropyl ethyldimonium ethosulfate, isostearyl ethyl imidonium ethosulfate, Quaternium-61, soyamidopropyl ethyldimonium ethosulfate, saffloweramidopropyl ethyldimonium ethosulfate, rapeseedamidopropyl ethyldimonium ethosulfate, apricotamidopropyl ethyldimonium ethosulfate, wheatgermamidopropyl ethyldimonium ethosulfate, canolamido propyl ethyl dimonium ethosulfate, and mixtures thereof.

10. The composition of claim 1 wherein said cationic compound further comprises an epoxypropyl chloride moiety.

11. The composition of claim 10 wherein said cationic compound is selected from the group consisting of Quaternium-62, rapeseedamidopropyl epoxypropyl dimonium chloride, and mixtures thereof.

12. The composition of claim 1 wherein said cationic compound further comprises an ester moiety selected from the group consisting of lauryl acetyl moieties and isostearyl acetyl moieties.

13. The composition of claim 12 wherein the cationic compound is selected from the group consisting of di-lauryl acetyl dimonium chloride, isostearamidopropyl lauryl acetodimonium chloride, and mixtures thereof.

14. The composition of claim 1 wherein said cationic compound further comprises at least one ethoxy chloride moiety.

15. The composition of claim 14 wherein the cationic compound is alkyl C12–C18 dimethyl ammonium ethoxy chloride.

16. The composition of claim 1 wherein the composition comprises from about 0.5% to about 10% of the non-silicone containing polymer.

17. The composition of claim 1 wherein said non-silicone containing polymer contains at least one monomer of vinyl pyrrolidone.

18. The composition of claim 17 wherein said non-silicone containing polymer is selected from the group consisting of PVP, PVP/VA Copolymer, Polyquaternium-11, and mixtures thereof.

19. The composition of claim 1 wherein said non-silicone containing polymer contains at least one monomer of hydroxyethylcellulose.

20. The composition of claim 19 wherein said non-silicone containing polymer is selected from the group consisting of Polyquaternium-4, Polyquaternium-10, and mixtures thereof.

21. The composition of claim 1 wherein said non-silicone containing polymer contains at least one chitin moiety.

22. The composition of claim 21 said non-silicone containing polymer is selected from the group consisting of Chitosan Lactate, Chitosan PCA, and mixtures thereof.

23. The composition of claim 1 further comprising a plasticizer.

24. The composition of claim 1 further comprising a plasticizer at a level of at least about 100% by weight of the non-silicone containing polymer.

25. The composition of claim 1 further comprising a plasticizer at a level of at least about 200% by weight of the polymer.

26. The composition of claim 1 further comprising a plasticizer that is an organic, hydrophilic compound.

27. The composition of claim 1 further comprising a plasticizer that is a humectant.

28. The composition of claim 26 wherein said plasticizer further comprises at least one hydroxyl group.

29. The composition of claim 28 wherein said plasticizer is selected from the group consisting of glycerine, propylene glycol, dipropylene glycol, diethylene glycol, and mixtures thereof.

30. The composition of claim 1 wherein the second solvent is selected from the group consisting of $C_1$–$C_3$ monohydric alcohols.

31. The composition of claim 30 wherein the monohydric alcohol is selected from the group consisting of consisting of ethanol, n-propanol, isopropanol, and mixtures thereof.

32. The composition of claim 30 wherein the first solvent is water.

33. The composition of claim 32 wherein the composition comprises about 40% or less of said $C_1$–$C_3$ monohydric alcohol.

34. The composition of claim 33 wherein the composition comprises about 16% or less of said $C_1$–$C_3$ monohydric alcohol.

35. The composition of claim 33 wherein the composition comprises about 6% or less of said $C_1$–$C_3$ monohydric alcohol.

36. A method of styling hair comprising applying to hair an effective amount of a composition according to claim 1.

* * * * *

UNITED STATES PATENT AND TRADEMARK OFFICE
CERTIFICATE OF CORRECTION

PATENT NO.    : 6,149,898
DATED         : November 21, 2000
INVENTOR(S)   : Peffly et al.

It is certified that error appears in the above-identified patent and that said Letters Patent is hereby corrected as shown below:

Column 4,
Line 30, "H2OLD" should read -- $H_2OLD$ --.
Line 51, 284971" should read -- 28-4971 --.

Column 9,
Line 42, "≦50" should read -- ≤50 --.
Line 50, "≦30" should read -- ≤30 --.

Column 18,
Line 59, "R" should read -- R''' --.

Column 20,
Line 46, "flve" should read -- five --.

Column 21,
Line 64, "(1)" should read -- (I) --.

Column 23,
Line 37, "can position" should read -- can composition --.

Signed and Sealed this

Fourteenth Day of October, 2003

JAMES E. ROGAN
*Director of the United States Patent and Trademark Office*